(12) United States Patent
Castellano

(10) Patent No.: US 7,744,513 B2
(45) Date of Patent: Jun. 29, 2010

(54) LEG LIFT DEVICE AND ASSOCIATED METHOD

(76) Inventor: Bradley Castellano, 11875 Rosalinda Ct., Fort Myers, FL (US) 33912

( * ) Notice: Subject to any disclaimer, the term of this patent is extended or adjusted under 35 U.S.C. 154(b) by 0 days.

(21) Appl. No.: 12/120,430

(22) Filed: May 14, 2008

(65) Prior Publication Data

US 2009/0082180 A1 Mar. 26, 2009

Related U.S. Application Data

(60) Provisional application No. 60/974,798, filed on Sep. 24, 2007.

(51) Int. Cl.
- *A63B 71/00* (2006.01)
- *A63B 25/00* (2006.01)
- *A63B 23/10* (2006.01)
- *A43B 3/16* (2006.01)
- *A61F 5/00* (2006.01)

(52) U.S. Cl. .......................... 482/139; 482/75; 482/79; 36/7.1 R; 36/15; 36/110; 602/23

(58) Field of Classification Search ................... 482/79, 482/105, 74, 75, 139, 148; 36/15, 7.1 R, 36/7.5, 11.5, 136, 110; 601/27, 28; 602/23, 602/27–29
See application file for complete search history.

(56) References Cited

U.S. PATENT DOCUMENTS

| | | | |
|---|---|---|---|
| 2,545,910 A * | 3/1951 | Aprile | 36/132 |
| 3,156,988 A | 11/1964 | Rause | |
| 3,713,437 A * | 1/1973 | Wiedmer | 601/27 |
| 3,905,135 A * | 9/1975 | Debusk | 36/110 |
| 4,176,459 A * | 12/1979 | Perser et al. | 33/515 |
| 4,217,706 A * | 8/1980 | Vartanian | 36/110 |
| 4,510,700 A * | 4/1985 | Brown | 36/44 |
| 4,693,019 A * | 9/1987 | Kim | 36/7.3 |
| 4,972,610 A | 11/1990 | Tong | |
| 5,070,868 A * | 12/1991 | Hepburn et al. | 602/27 |
| 5,177,883 A | 1/1993 | Darby | |
| 5,452,527 A * | 9/1995 | Gaylord, Jr. | 36/110 |
| 5,582,579 A * | 12/1996 | Chism et al. | 601/27 |
| 5,713,820 A * | 2/1998 | Carbone | 482/79 |
| 2002/0178621 A1* | 12/2002 | Darby | 36/140 |
| 2003/0200676 A1* | 10/2003 | Gross | 36/15 |
| 2005/0131324 A1* | 6/2005 | Bledsoe | 602/23 |
| 2008/0168681 A1* | 7/2008 | Andersen et al. | 36/100 |

* cited by examiner

*Primary Examiner*—Loan H Thanh
*Assistant Examiner*—Allana Lewin
(74) *Attorney, Agent, or Firm*—Adrian D. Battison; Ade & Company Inc.

(57) ABSTRACT

A leg lift device is provided for attachment to a shoe. The leg lift device includes a sole, an optional lift insert and a shoe receiver attached to the sole. The shoe receiver includes a first section to engage a toe of a shoe and a second section to engage a heel of a shoe. The device also includes an attachment strap. A selected method is also provided.

10 Claims, 4 Drawing Sheets

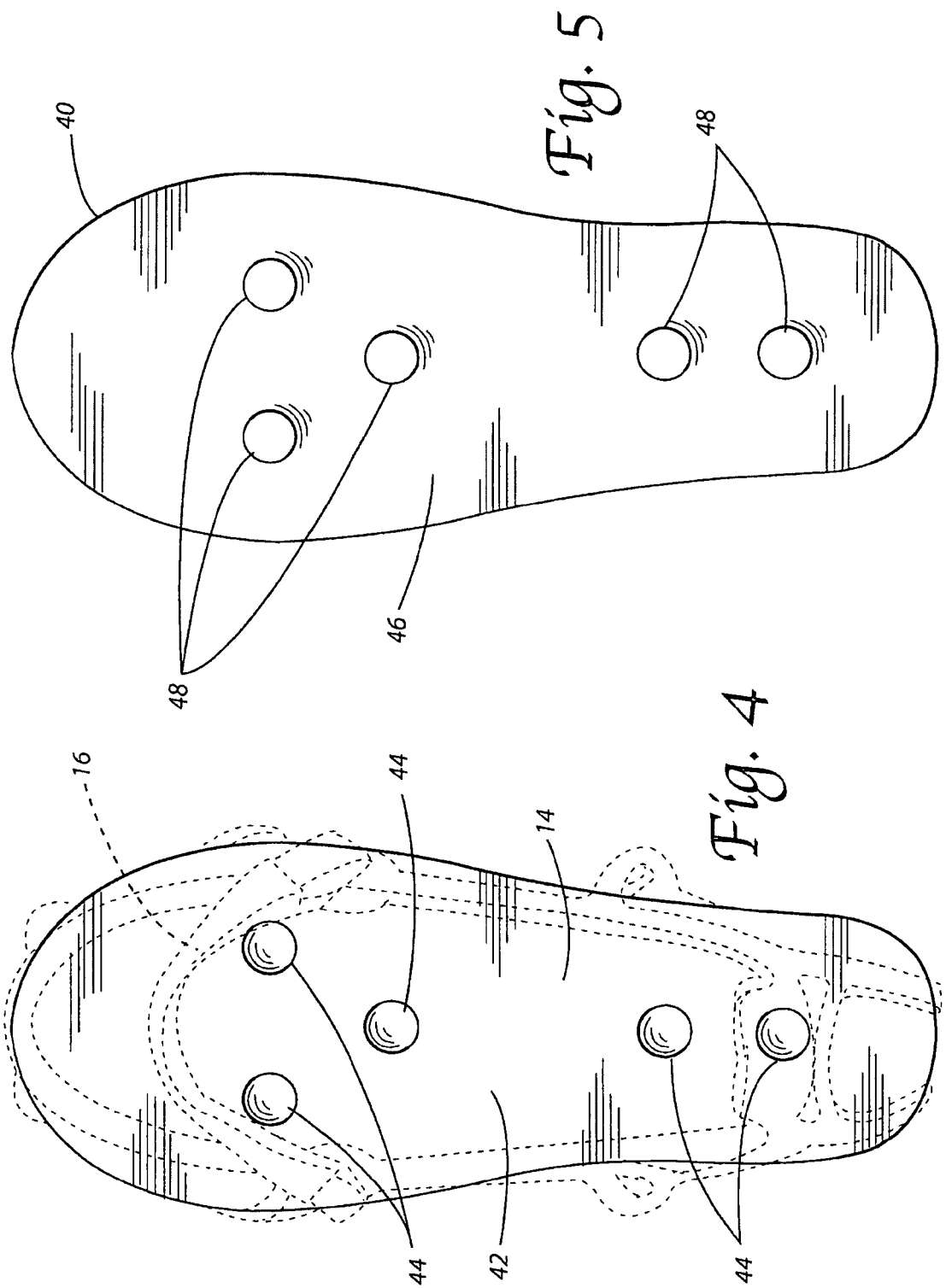

LEG LIFT DEVICE AND ASSOCIATED METHOD

This application claims the benefit of U.S. Provisional Patent Application Ser. No. 60/974,798 filed on 24 Sep. 2007.

TECHNICAL FIELD OF THE INVENTION

The present invention relates generally to the physical rehabilitation field and, more particularly, to a leg lift device and associated method for reducing the physiological strain placed on the knees, hip and back when walking with a fracture walker, cast boot, thick soled wound healing shoe or the like.

BACKGROUND OF THE INVENTION

The recent use of fracture orthotic walkers has been a very common therapy modality for multiple types of lower leg and foot injuries. A frequent complaint of patients that are utilizing this device is that it causes a marked inequality of limb length resulting in pain or injury to other areas of the body. Knee, hip and even back pain are frequently an untoward effect of these walker boots. A similar problem arises in patients or individuals walking in a cast boot or a thick soled wound healing shoe. The added height of the cast boot or wound healing shoe worn on the foot of an individual's injured limb compared to a standard shoe worn on the foot of an individual's uninjured limb creates an unlevel condition that produces stress upon various body joints and the back. Inside shoe devices, such as heel lifts, are less physiological in function and often do not provide adequate lift to completely compensate for the induced limb length discrepancy. Accordingly, such devices are not true solutions for the problem.

Recognizing this, prosthetists and physicians are currently treating lower limb length discrepancies by fixing a block or platform to the sole of a shoe with adhesives. It should be appreciated that this is a permanent method of applying a platform resulting in one pair of corrective shoes. This usually requires a visit to a prosthetist or shoe maker to be fitted for and to fabricate the corrective shoe. Following treatment, the corrective shoe can no longer be used by the individual. This waste and expense is avoided using the device and method of the present invention.

More specifically, the present invention is easily applied temporarily to a shoe by the consumer or patient. No special shoe or shoes need to be purchased. Further, following recovery, the individual or patient can simply remove the device from the shoe thereby restoring the shoe for normal use.

SUMMARY OF THE INVENTION

In accordance with the purposes of the present invention as described herein, a leg lift device is provided for attachment to a shoe. The leg lift device comprises a sole, an optional lift insert and a shoe receiver attached to the sole. The receiver includes a first section to engage a toe of the shoe and a second section to engage a heel of the shoe. In addition, the device may include an attachment strap connected to the sole or the shoe receiver. Typically the attachment strap includes a fastener such as a hook and loop fastener.

More specifically describing the invention the shoe receiver is an open web or mesh made from an elastomeric material. Such a material may be selected from a group consisting of thermoplastic elastomer (TPE), rubber, latex or other synthetic elastomer and combinations thereof suitable for the intended purpose.

Further describing the invention the sole includes at least two recesses. The lift insert includes at least two projections that are received in and engage the recesses in the sole. Each lift insert has a profile substantially matching the sole and a thickness of between about 1.0 and about 5.0 cm and more typically between about 1.0 and about 2.0 cm. Lift inserts of different thicknesses or heights may be interchangeably connected to the sole in order to provide a leg lift device of the desired height to match the height of the fracture walker, cast boot or fixed soled wound healing shoe worn on the other foot of the user.

In accordance with an additional aspect of the present invention, a method is provided for reducing the physiological strain on an individual associated with walking when a fracture walker, cast boot or thick soled wound healing shoe is worn on a first foot by an individual. The method may be broadly described as comprising detachably connecting a leg lift device to a shoe worn on the second foot of an individual. The method may be further described as including the step of adjusting a height of a leg lift device worn on the second foot to substantially match the height of the fracture walker, cast boot or wound healing shoe worn on the first foot. This is done by selecting a lift insert of desired height or thickness from a series of lift inserts of differing heights and securing the selected lift insert to the sole of the leg lift device.

Still further, the method may be described as including the step of inserting a shoe to be worn on the second foot into the leg lift device and attaching the leg lift device to the shoe. Further, the method may include removing the shoe from the leg lift device as desired. Still further, the method may include inserting a different shoe into the leg lift device and attaching the leg lift device to the different shoe. The device may be adjusted to compensate for any difference in sole height between the first and second shoes by changing the lift insert used in the device. In this way, it is possible for the user to increase the height of any number of shoes owned by the user to substantially match the height of the fracture walker, cast boot or thick soled wound healing shoe so as to allow the user to walk in a level attitude using many different shoes owned by the individual and appropriate for wear at a particular occasion.

In the following description there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings:

FIG. 4 is a top plan view of the sole of the device showing the recesses or apertures provided in the face thereof;

FIG. 5 is a bottom plan view of a lift insert for the device showing the projections provided on the bottom face thereof that are received in the recesses provided in the upper face of the sole.

Reference will now be made in detail to the present preferred embodiment of the invention, an example of which is illustrated in the accompanying drawings.

DETAILED DESCRIPTION OF THE PREFERRED EMBODIMENTS OF THE INVENTION

Figure 1:
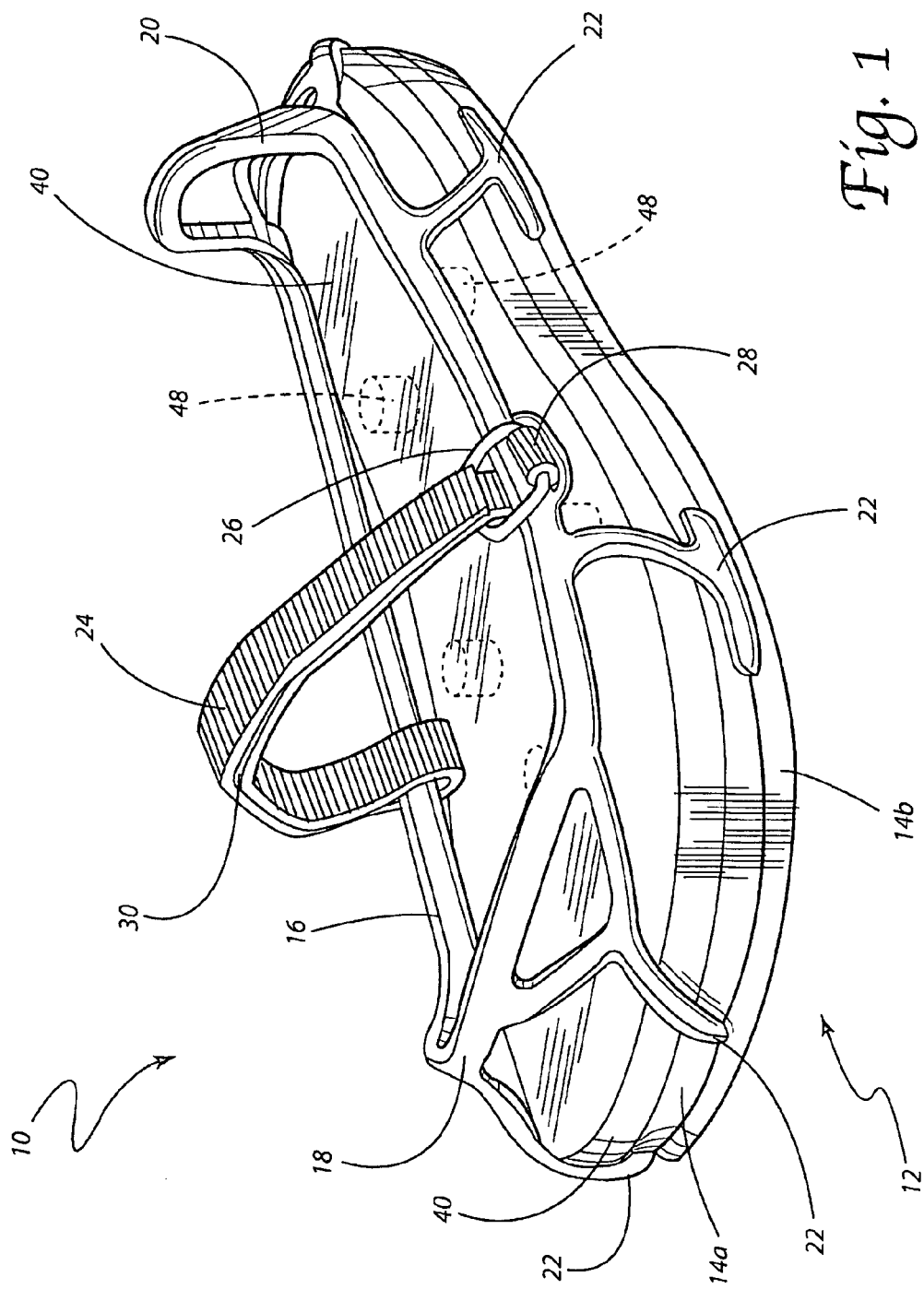
FIG. 1 is a perspective view of the leg lift device of the present invention.
Figure 2:
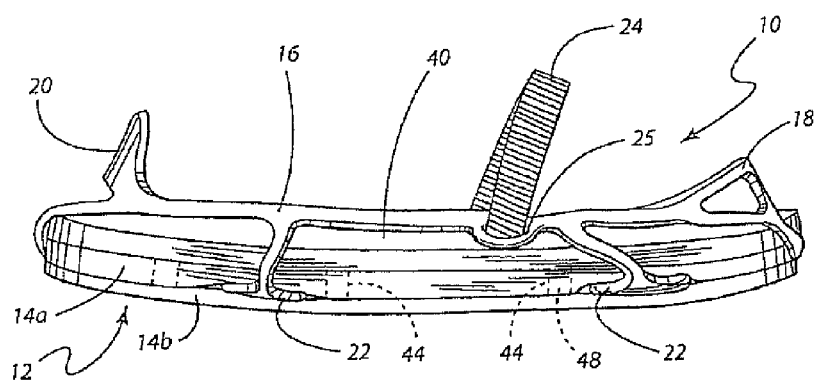
FIG. 2 is a right side elevational view of the leg lift device illustrated in FIG. 1.

Reference is now made to FIGS. 1 and 2 illustrating the leg lift device 10 of the present invention. The leg lift device 10 comprises a sole 12, including first and second sections 14a, 14b, and a shoe receiver 16. The shoe receiver 16 may take the form of a mesh or web and includes a first section 18 to engage a toe of a shoe and a second section 20 to engage a heel of a shoe (see also FIG. 3). Typically the sole 12, including both sections 14a, 14b is made from a material selected from a group consisting of ethylene vinyl acetate (EVA), polyphenylene ether (PPE) rubber and polymeric foam materials. The shoe receiver 16 is made from an elastomeric material. Such a material may be selected from a group consisting of thermoplastic elastomer (TPE), rubber, latex or other synthetic elastomeric material suitable for the intended purpose.

As illustrated, the shoe receiver 16 includes a series of lugs 22 that are secured to the sole 12 at spaced points between the sole sections 14a, 14b. The shoe receiver 16 may be secured to the sole 12 at the lugs 22 by adhesive, heat welding or other appropriate means.

As further illustrated in FIGS. 1 and 2, the leg lift device 10 also includes a strap 24. The strap 24 is connected at a first end to a metal loop 26 that is secured to the shoe receiver 16 by the connector 28. The strap 24 is then looped through an aperture or opening 25 (see FIG. 2) in the opposite side of the shoe receiver 16. A fastener 30 such as a hook and loop fastener allows the strap 24 to be secured in position.

Figure 6:
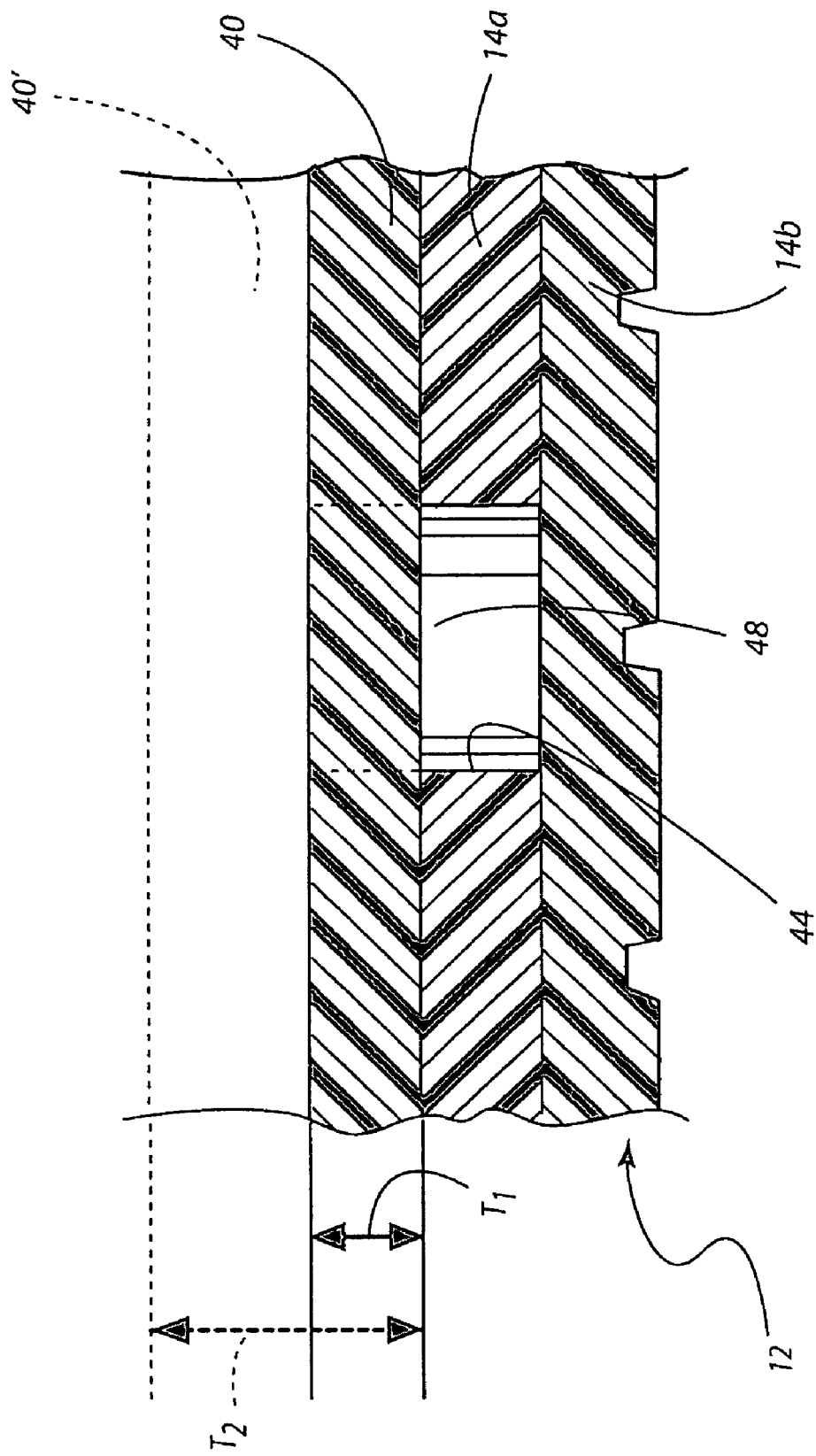
FIG. 6 is a detailed cross sectional view showing one of the projections on the lift insert received in one of the recesses or apertures provided in the sole.

As best illustrated in FIGS. 2-5, it should be appreciated that the leg lift device 10 includes an optional lift insert 40 also made from a cushioning, elastomeric material. More specifically, each lift insert 40 includes a profile or outline matching the sole 12. As best illustrated in FIG. 4, the top face 42 of the sole 12 (and more specifically, sole section 14a) includes two or more spaced recesses or apertures 44. As best illustrated in FIG. 5, the bottom face 46 of the lift insert 40 includes two or more spaced projections 48. When the lift insert 40 is property connected to the sole 12 of the device 10, the projections 48 are received within and engage the apertures 44 and the outer periphery of the insert 40 and the sole 12 match (see also FIG. 6).

Each insert 40 may have a thickness or height of between about 1.0 and about 5.0 cm and more typically between about 1.0 and about 2.0 cm. Each device 10 may include multiple lift inserts 40 with each insert having a different thickness or height. Each of the lift inserts 40 may be interchangeably connected to the sole 12 of the device 10. Thus, by selecting a lift insert 40 of proper height, it is possible to match the height of the device 10 to the height of the fracture walking cast boot or healing shoe and thereby fully compensate for the leg length discrepancy characteristic of that device. For example, FIG. 6 discloses a first lift insert 40 of thickness $T_1$ in full line and a second lift insert 40' of greater height or thickness $T_2$ in phantom line.

Figure 3:
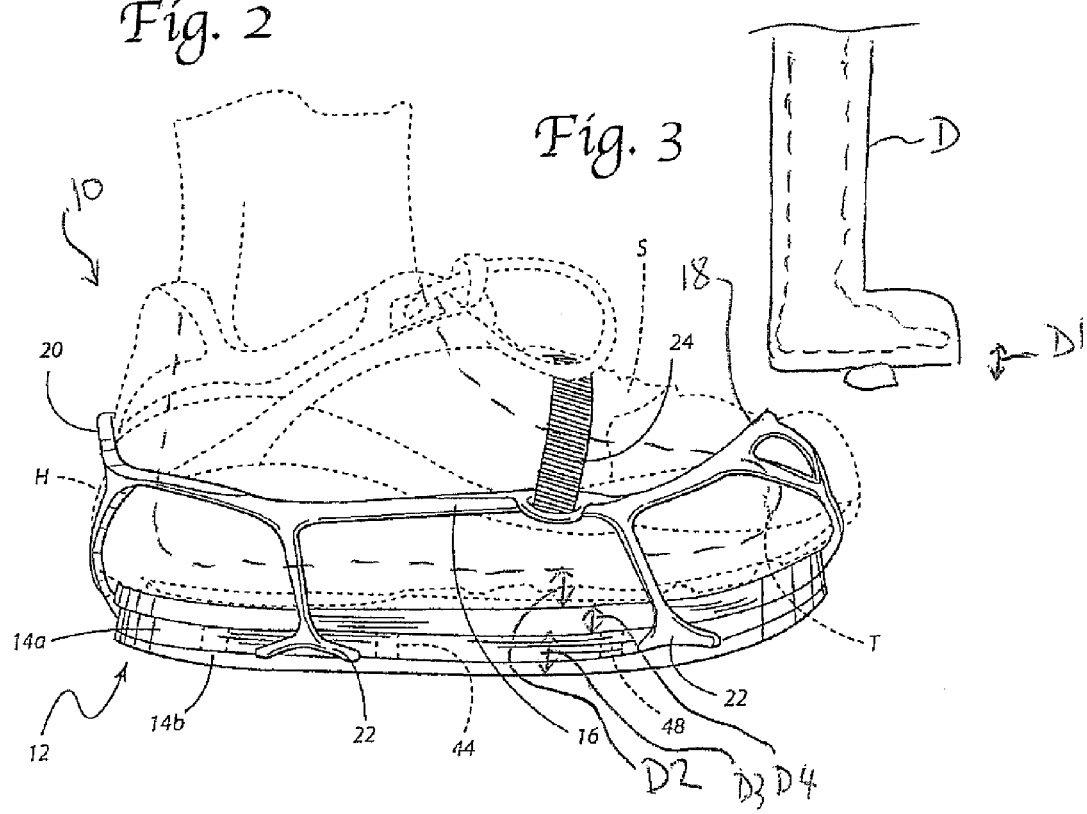
FIG. 3 shows in combination the therapeutic device to be used on the leg to be treated together with a left side elevational view of the leg lift device holding a shoe of a user.

In use, the strap 24 is opened and the leg lift device 10 is connected to a shoe S (see FIG. 3). More specifically, the shoe S is positioned with the sole of the shoe against the lift insert 40. As noted, the toe T of the shoe S is engaged under the first section 18 of the shoe receiver 16 while the heel H is engaged by the second section 20. Since the shoe receiver 16 is made from elastomeric material, it readily stretches to receive the shoe S. The resilient memory of the elastomeric material then ensures that the shoe receiver 16 tightly engages the shoe S so as to hold the shoe S firmly on the shoe support 14. The strap 24 is then pulled tight and fastened by means of the hook and loop fastener 30 in order to complete the connection of the leg lift device 10 to the shoe S.

The leg lift device 10 of the present invention is used in a method of reducing the physiological strain on an individual associated with walking when a fracture boot, cast boot or thick soled wound healing shoe is worn on a first foot by that individual. The method comprises detachably connecting the leg lift device 10 to the shoe S worn on the second foot of the individual. Toward this end, the method includes adjusting the height of the leg lift device 10 worn on the second foot so that the combined sole height of the shoe S and the device 10 substantially matches the height of the fracture walker, cast boot or wound healing shoe worn on the first foot. This is done by connecting a lift insert 40 of desired height to the sole 12 so as to form a device 10 of overall height substantially matching the height of the fracture walker, cast booth or thick soled wound healing shoe worn on the first foot by the individual. By providing a shoe height for the off leg substantially corresponding to the height of the fracture walker, cast booth or thick soled wound healing shoe for the leg undergoing treatment, the walking height between the two legs is substantially leveled. This reduces or substantially eliminates strain that would otherwise be placed on the joints of the individual including the knee and hip as well as the back.

Advantageously, the leg lift device 10 is easily detachable and may be used on a number of different shoes thereby allowing the user to wear different shoes for different occasions as desired without permanently altering any shoe. Significantly, the device 10 allows for use even when the selected shoes are of totally different sole heights. For example, a fracture walker worn on the foot of an injured limb has an overall sole height of 10 cm. A tennis shoe worn on the foot of the uninjured limb has an overall sole height of 3 cm. To compensate for the height of the fracture walker, the device 10 is provided with an overall sole height of 7 cm when worn with the 3 cm tall tennis shoe. Where the sole 12 of the device has a sole height or thickness of 3 cm, the lift insert 40 used has a height or thickness of 4 cms.

If the user later decides to wear a dress shoe having a sole height of 5 cm instead of the tennis shoe with a sole height of 3 cm, the device 10 is able to compensate for the difference. Specifically, the lift insert 40 with a height of 4 cms is removed from the device 10 and replaced with a lift insert 40 having a sole height of 2 cm.

Advantageously, the device 10 and method of the present invention allow, the user flexibility of wearing different shoes as desired and no shoe is permanently altered. Since the shoes are not permanently modified, they may still be used following treatment and removal of the fracture walker, cast boot or thick soled wound healing shoe.

In FIG. 3 the therapeutic device indicated at D and defined by the fracture walking cast, boot or healing shoe is arranged such that the foot of the first leg of the patient is supported at a position spaced from the ground by a first distance D1 when walking. The shoe S defines a second distance D2 of the foot of the second leg from a bottom of the shoe.

The sole plate 12 defines a first lift distance D3 by which the shoe is raised from the ground. The lift insert piece 40 defines a thickness or a second lift distance D4 by which the shoe is raised from the ground. As explained previously, if the optional lift insert 40 is used, the first distance D1 is substantially equal to the sum of the second distance D2 and the first lift distance D3. If the lift insert 40 is not used, the first distance D1 is substantially equal to the sum of the second distance D2, the first lift distance D3 and the second lift distance D4 so as to reduce the physiological strain placed on the knees, hip and back of the patient when walking.

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. Apparatus for therapeutic treatment of a patient having two legs, a first one of which requires the therapeutic treatment, the apparatus comprising:
    a therapeutic device for attachment to the first leg of the patient for applying a therapeutic effect to the first leg, the therapeutic device being arranged such that the foot of the first leg of the patient is supported at a position spaced from the ground by a first distance when walking;
    a shoe for attachment to the foot of a second one of the legs of the patient to be worn when walking, the shoe defining a second distance of the foot of the second leg from a bottom of the shoe; and
    a leg lift device for attachment to the shoe, comprising:
    a sole plate arranged to engage underneath the shoe for engaging the ground beneath the shoe, the sole plate defining a first lift distance by which the shoe is raised from the ground;
    a flexible shoe receiver attached to said sole plate around a periphery of said sole plate, said receiver including a first section to releasably engage over a toe of the shoe and a second section to releasably engage around a heel of the shoe such that the flexible shoe receiver engages around the shoe to hold the sole plate onto the shoe to remain in place between the shoe and the ground during walking, the shoe being readily removable from the flexible shoe receiver;
    and a lift insert piece arranged to be inserted between the shoe and the sole plate and arranged to remain in place during walking, the lift insert piece defining a second lift distance by which the shoe is raised from the ground;
    the therapeutic device being arranged such that:
        either the first distance is substantially equal to the sum of the second distance and the first lift distance;
        or the first distance is substantially equal to the sum of the second distance, the first lift distance and the second lift distance;
    so as to reduce the physiological strain placed on the knees, hip and back of the patient when walking.

2. The apparatus of claim 1, wherein there is provided between said sole plate and said lift insert piece at least one cooperating engagement arrangement to hold the lift insert piece in place on said sole plate and beneath said shoe during walking.

3. The apparatus of claim 2, wherein said cooperating engagement arrangement comprises a recess on one of said sole plate and said lift insert piece and a cooperating projection on the other of said sole plate and said lift insert piece.

4. The apparatus of claim 3, wherein there are at least two cooperating engagement arrangements each comprises a recess on one of said sole plate and said lift insert piece and a cooperating projection on the other of said sole plate and said lift insert piece.

5. The apparatus of claim 1, wherein said shoe receiver is an open web made from an elastomeric material including a top band engaged around the shoe and a plurality of separate lugs extending from the top band to the sole plate.

6. The apparatus of claim 5, further including an attachment strap connected across the top band from one side to an opposed side.

7. The apparatus of claim 5, wherein said shoe receiver is made from a material selected from a group consisting of thermoplastic elastomer (TPE), rubber, latex, synthetic elastomer and combinations thereof.

8. The apparatus of claim 1, wherein the apparatus includes a single lift insert piece.

9. The apparatus of claim 1, wherein the apparatus includes a series of lift insert pieces.

10. The apparatus of claim 1, wherein the apparatus includes a series of lift insert pieces of different thicknesses.

* * * * *